United States Patent [19]  
Luebbe et al.

[11] Patent Number: 4,781,917  
[45] Date of Patent: Nov. 1, 1988

[54] ANTIPERSPIRANT GEL STICK

[75] Inventors: John P. Luebbe, Lawrenceburg, Ind.; Paul R. Tanner, Cincinnati; Richard D. Farris, West Chester, both of Ohio

[73] Assignee: The Proctor & Gamble Company, Cincinnati, Ohio

[21] Appl. No.: 67,573

[22] Filed: Jun. 26, 1987

[51] Int. Cl.$^4$ ................................. A61K 7/32
[52] U.S. Cl. ......................... 424/65; 424/66; 424/67; 424/68; 514/494; 514/554; 514/740; 514/741; 514/828; 514/873; 514/944; 514/949
[58] Field of Search .............. 424/65, 66, 67, 68; 514/494, 554, 740, 741, 828, 873, 944, 949

[56] References Cited

U.S. PATENT DOCUMENTS

| | | | |
|---|---|---|---|
| 4,120,948 | 10/1978 | Shelton | 424/68 |
| 4,202,879 | 5/1980 | Shelton | 424/68 |
| 4,346,079 | 8/1982 | Roehl | 424/68 |
| 4,518,582 | 5/1985 | Schamper et al. | 424/68 |
| 4,617,185 | 10/1986 | DiPietro | 424/DIG. 5 |
| 4,673,570 | 6/1987 | Soldati | 424/68 |
| 4,708,863 | 11/1987 | Bews et al. | 424/65 |

Primary Examiner—Morton Foelak  
Assistant Examiner—S. A. Acquah  
Attorney, Agent, or Firm—David K. Dabbiere; Steven J. Goldstein; Douglas C. Mohl

[57] ABSTRACT

Disclosed are antiperspirant gel stick compositions substantially free of unbound water comprising from about 5 to about 50% of a solubilized antiperspirant active, from about 7% to about 35% of intermediate polarity emollients, from about 1% to about 5% of a benzylidene sorbitol, from about 15% to about 75% of a polar solvent, from about 1% to about 20% of a coupling agent and from about 0.5% to about 10% of a bufferieng agent. These antiperspirant gel sticks provide very stable antiperspirant compositions with good efficacy as well as excellent cosmetic anesthetics which are further characterized by their ease of manufacture. Also disclosed is a method for the manufacture of these gel sticks as well as a method for treating or preventing perspiraton and malodor associated with human underarm perspiration.

16 Claims, No Drawings

ANTIPERSPIRANT GEL STICK

BACKGROUND OF THE INVENTION

The present invention relates to stick-type antiperspirant compositions. More particularly it relates to improved gel-type antiperspirant sticks, a method for their manufacture and also to methods for treating or preventing perspiration and malodor associated with human underarm perspiration.

There are three main types of such stick formulations: compressed powder sticks, gel sticks, and wax sticks. While each of these formulation types may have advantages in certain use situations, each also has disadvantages. For example, compressed powder sticks are often brittle and hard, and leave a cosmetically-unacceptable dust upon application. Gels, while offering very good aesthetic characteristics, may be unstable due to interaction of the soap gelling agents typically used to solidify such sticks with the stick's "active" material (e.g., the astringent metallic salts used in antiperspirant sticks). Wax-based formulations can also yield cosmetically-unacceptable products due to such factors such as hardness, greasiness, and stickiness. The opacity of such wax sticks, and the residue created in their use, may also be aesthetically undesirable.

Many stick formulations have been described in the literature which attempt to maintain the desirable cosmetic and aesthetic attributes of gel sticks, while minimizing their disadvantages. For example, antiperspirant gel sticks, using dibenzaldehyde monosorbitol acetal (herein "DBMSA") as a gelling agent, are described in U.S. Pat. No. 4,154,816, Roehl, et al., issued May 15, 1979, U.S. Pat. No. 4,346,079, Roehl, issued Aug. 24, 1982, and U.S. Pat. No. 4,518,582, Schamper, et al., issued May 21, 1985. Deodorant sticks using DBMSA are described in Japanese Pat. No. 50/52,007, published Apr. 8, 1975. Nevertheless, it has been found that such DBMSA sticks, while avoiding the use of soaps, may produce products with aesthetically unacceptable stickiness. Further, these sticks have relatively poor efficacy and contain high levels of ethanol which leads to skin irritation. This high level of ethanol also leads to shrinkage and weight loss of the packaged antiperspirant gel stick due to the volatility of ethanol.

The gel sticks of the prior art require very high processing temperatures as well as short active/DBMSA contact time which leads to product instability and to processing difficulties in large scale product manufacture. DBMSA is unstable in the presence of acid salts (such as antiperspirant actives). This instability is accentuated at high processing temperatures. The gel sticks of the present invention can be manufactured at lower processing temperatures, thereby allowing for longer active/DBMSA contact time, thereby producing a much more stable and satisfactory product.

Further, while the prior art teaches the addition of basic metal salts for stability, the present invention additionally provides a gel matrix of decreased polarity which significantly enhances the stability of the final product. The solid get sticks of the present invention provide very stable antiperspirant gel stick compositions with good efficacy as well as excellent cosmetics and aesthetics which are further characterized by their ease of manufacture.

It is therefore an object of the present invention to provide antiperspirant gel sticks which have good antiperspirant efficacy. It is still a further object to provide optically clear or translucent gel sticks which are cosmetically acceptable. A still further object of the present invention is to provide gel sticks which are stable and easy to formulate and manufacture. A still further object is to provide gel sticks which are non-sticky. A still further object is to provide gel sticks which contain relatively low levels of ethanol to minimize skin irritation, stinging and burning.

These and other objects of the present invention will become readily apparent from the detailed description which follows.

All percentages and ratios used herein are by weight unless otherwise specified.

SUMMARY OF THE INVENTION

The present invention relates to antiperspirant gel stick compositions which are substantially free of unbound water. These gel sticks comprise:
(a) from about 5% to about 50% of a solubilized antiperspirant active;
(b) from about 7% to about 35% of an intermediate polarity emollient;
(c) from about 1% to about 5% of a benzylidene sorbitol;
(d) from about 15% to about 75% of a polar solvent;
(e) from about 1% to about 20% of a coupling agent; and
(f) from about 0.5% to about 10% of a buffering/pH adjustment agent.

The present invention also relates to a process for the manufacture of these gel sticks by:
(a) preparing a premix comprising:
  (i) from about 1% to about 40% of an antiperspirant active;
  (ii) from about 10% to about 98% of water; and
  (iii) from about 1% to about 40% of a polyhydric alcohol; removing said water, thereby forming a solubilized antiperspirant active and then heating the solubilized antiperspirant active to a temperature of from about 130° F. (54° C.) to about 165° F. (74° C.);
(b) preparing a main mix comprising the remaining components and heating said main mix to a temperature of from about 170° F. (77° C.) to about 225° F. (107° C.);
(c) combining said solubilized antiperspirant active and said main mix in a ratio of solubilized active to main mix of from about 1:19 to about 1:1 for from about 0.2 minutes to about 5 minutes; and
(d) pouring said composition into stick form.

These gel stick compositions have good antiperspirant efficacy as well as excellent cosmetics and aesthetics, Further, these gel sticks are substantially free of unbound water. The term "substantially free of unbound water" as used herein, means that less than 1% by weight of water not chemically bound to the materials is present in the gel stick composition.

DETAILED DESCRIPTION OF THE INVENTION

Solubilized Antiperspirant Actives

The antiperspirant composition of the present invention comprises from about 5 to about 50% of the solubilized active solution. The antiperspirant actives useful in the compositions of the present invention are antiperspirant actives soluble in the polyhydric alcohol present in the stick composition. The terms "soluble" and "solubilized", as used herein, mean that the antiperspirant active is dissolved in and/or colloidally dispersed (submicron particle size) in the polyhydric alcohol utilized in the composition being prepared to give a transparent or semitransparent liquid. Typically the transparency of the liquid is such that more than 50%, preferably more than 75%, of 500 nm light is transmitted through the liquid as measured by a standard UV-visible absorption instrument (relative to the polyhydric alcohol without the antiperspirant active). Antiperspirant actives soluble in alcohols are known, having been disclosed, for example, in U.S. Pat. No. 4,137,306, to Rubino et al, issued Jan. 30, 1979, the disclosure of which is incorporated herein by reference in its entirety.

The solubilized antiperspirant active contains a ratio of solvent to active of from about 0.8:1 to about 2.5:1 preferably 1:1 to about 1.5:1. The solubilized active is formed by dissolving the active in, for example, an equal weight of water, mixing in the polar organic solvent and removing the water as described below.

1. Antiperspirant Salt

Preferred antiperspirant actives useful herein include the following: Polyhydroxy complexes of basic aluminum salts as described in U.S. Pat. No. 3,420,932 to Jones et al, issued Jan. 7, 1969; U.S. Pat. No. 3,359,169, to Slater et al, issued Dec. 19, 1967; U.S. Pat. No. 3,523,130, to Jones et al, issued Aug. 4, 1970; U.S. Pat. No. 3,507,896, to Jones et al, issued Apr. 21, 1970; U.S. Pat. No. 3,873,686, to Beekman, issued Mar. 25, 1975; U.S. Pat. No. 3,876,758, to Beekman, issued Apr. 8, 1975; and Britain Patent Specification No. 1,159,685, to Armour Pharmaceutical Co., published July 30, 1969 (all of these disclosures being incorporated herein by reference in their entirety) and commercially-available as Rehydrol and Rehydrol ll (supplied by Reheis Chemical Co.). Polyhydroxy derivatives of zinc and zirconium complexes of basic aluminum halides as described in U.S. Pat. No. 3,405,153, to Jones et al, issued Oct. 8, 1968; U.S. Pat. No. 3,555,146, to Jones et al, issued Jan. 12, 1971; Britain Patent Specification No. 1,159,686, to Jones et al, published July 30, 1969 (all these disclosures being incorporated herein by reference in their entirety). Zirconyl hydroxychloride salts, especially zironium-aluminum-glycine complexes ("ZAG complexes"), as described in the following patent documents, all incorporated by reference herein in their entirety: Belgium Patent Specification No. 825,146, to Schmitz, issued Aug. 4, 1975; U.S. Pat. No. 2,814,585, to Daley, issued Nov. 26, 1957; U.S. Pat. No. 3,679,068, to Luedders et al, issued Feb. 12, 1974; U.S. Pat. No. 4,017,599, to Rubino, issued Apr. 12, 1977; U.S. Pat. 4,120,948, to Shelton, issued Oct. 17, 1978; and Britain Patent Specification 2,144,992, to Callaghan et al, published Mar. 20, 1985. Aluminum chloride and aluminum chlorhydroxide ("ACH") salts as described in the following documents, all incorporated by reference herein in their entirety: U.S. Pat. No. 3,887,692, to Gilman, issued June 3, 1975; U.S. Pat. No. 3,904,741, to Jones et al, issued Sept. 9, 1975; U.S. Pat. No. 4,359,456, to Gosling et al, issued Nov. 16, 1982; Britain patent specification No. 2,048,229, to Fitzgerald et al, published Dec. 10, 1980; and Britain patent specification No. 1,347,950, to Shin et al, published Feb. 27, 1974.

Particularly preferred antiperspirant actives useful herein are those with enhanced efficacy due to improved molecular distributions, especially polyhydric alcohol solubilized ACH salts, polyhydric alcohol solubilized zirconyl hydroxychloride salts, and mixtures thereof (especially ZAG complexes), as described in copending U.S. patent application Ser. No 061,260. (P&G Case 3672), by Tanner et al., "Liquid Antiperspirant Actives and Processes for Preparing the Same", filed June 11, 1987 (incorporated by reference herein in its entirety). Aluminum chlorhydroxide salts, zirconyl hydroxychloride salts, and mixtures thereof having improved molecular distributions are known, having been disclosed, for example, in the following documents, all incorporated by reference herein in their entirety: U.S. Pat. No. 4,359,456, to Gosling et al, issued Nov. 16, 1982; European Patent Application Publication No. 6,739, to Unilever Limited, published Jan. 9, 1980; European Patent Application Publication No. 183,171, to Armour Pharmaceutical Company, published June 4, 1986; British Patent Specification No. 2,048,229, to The Gillette Company, published December 10, 1980; European Patent Application Publication No. 191,628, to Unilever PLC, published August 20, 1986; and British Patent Specification No. 2,144,992 to the Gillette Company, published Mar. 20, 1985. Antiperspirant actives with enhanced efficacy due to improved molecular distribution are also described in European Patent Application Publication No. 7,191, to Unilever Limited, published Jan. 23, 1980, incorporated by reference herein in its entirety.

The improved molecular distribution is determined by the known analysis method called gel permeation chromatography. This analysis method is described, for example, in several of the above-incorporated patent specifications. It is preferred for purposes of the present invention that the antiperspirant active soluble in the polyhydric alcohol have enhanced efficacy due to improved molecular distribution having the ratio of peak 3 to peak 2 greater than about 0.1:1 as determined by gel permeation chromatography. This ratio, as is recognized by one skilled in the art, relates to the relative area under these two peaks as measured by the gel permeation chromatography analysis method.

2. Polyhydric Alcohol Solvents

The solvents used to solubilize the antiperspirant actives of the present invention are one or more polyhydric alcohols selected such that the polyhydric alcohol solubilized antiperspirant active is a liquid at room temperature. Typical liquid polyhydric alcohols for use in the compositions of the present invention include: 1,2-propylene glycol; 1,3-propylene glycol; 1,3-butylene glycol (1,3-butane-diol); glycerine (1,2,3-trihydroxy propane); 2-methyl-2,4-pentane-diol; and 2-ethyl-1,3-hexane-diol. Preferred for use herein is glycerine, propylene glycol, and mixtures thereof. Most preferred is 1,2-propylene glycol.

Emollients

The compositions of the present invention contain from about 7% to about 35% of one or more intermediate polarity emollient. Preferred intermediate polarity emollients of the present invention include di-n-butyl phtalate, diethyl sebacate, di-isopropyl adipate and ethyl ethyl carbomethyl phthalate, all of which are disclosed in U.S. Pat. No. 4,045,548 to Luedders et al, issued August 30, 1977, which is incorporated by reference herein. The most preferred intermediate polarity emollient is di-isopropyl adipate.

The compositions of the present invention can further comprise from about 1% to about 10%, preferably from about 4% to about 8% of optional non-polar emollients.

Emollients among those useful herein are described in 1 *Cosmetics, Science and Technology* 27–104 (M. Balsam and E. Sagarin, Ed.; 1972), and U.S. Pat. No. 4,202,879, to Shelton, issued May 13, 1980 (both incorporated by reference herein). Preferred optional emollients include non-polar fatty acids and fatty alcohol esters such as isopropyl myristate, isopropyl palmitate, PPG-2 myristyl ether propionate and hydrocarbons such as isohexadecane (e.g., Permethyl 101A supplied by Presperse). Most preferred is isohexadecane. Useful non-polar emollients also include volatile silicone oils, non-polar non-volatile emollients, and mixtures thereof. The term "volatile", as used herein, refers to those materials which have a measurable vapor pressure at ambient temperature.

Volatile silicone oils useful in the cosmetic stick compositions of the present invention are preferably cyclic or linear polydimethylsiloxanes containing from about 3 to about 9, preferably from about 4 to about 5, silicon atoms. The following formula illustrates cyclic volatile polydimethylsiloxanes useful in the cosmetic stick compositions disclosed herein:

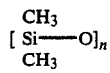

wherein n equals about 3 to about 7. Linear polydimethylsiloxanes contain from about 3 to about 9 silicon atoms per molecule and have the following general formula:

wherein n equals about 1 to about 7. Linear volatile silicone materials generally have viscosities of less than about 5 centistokes at 25° C. while cyclic materials typically have viscosities of less than about 10 centistokes. A description of various volatile silicone oils is found in Todd, et al., "Volatile Silicone Fluids for Cosmetics", *Cosmetics & Toiletries*, 91, pages 27–32 (1976), the disclosures of which are incorporated by reference herein in their entirety.

Examples of preferred volatile silicone oils useful herein include: Dow Corning 344, Dow Corning 345, and Dow Corning 200 (manufactured by the Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

Non-volatile silicone oils useful as an emollient material include polyalkylsiloxanes, polyalkylarysiloxanes, and polyethersiloxane copolymers. The essentially non-volatile polyalkyl siloxanes useful herein include, for example, polydimethyl siloxanes with viscosities of from about 5 to about 100,000 centitokes at 25° C. Among the preferred non-volatile emollients useful in the present compositions are the polydimethyl siloxanes having viscosities from about 10 to about 400 centistokes at 25° C. Such polyalkyl siloxanes include the Vicasil series (sold by General Electric Company) and the Dow Corning 200 series (sold by Dow Corning Corporation). Polyalkylaryl siloxanes include poly methylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is avilable as SF-1066 organosilicone surfactant (sold by General Electric Company). Polysiloxane ethylene glycol ether copolymers are preferred copolymers for use in the present compositions.

Benzylidene Sorbitol

The compositions of this invention also include from about 1% to about 5%, preferably from about 2% to about 4% of a benzylidene sorbitol, which serves as a gelling agent for the antiperspirant stick. The level of these agents are chosen so as to provide the appropriate stick hardness and the appropriate level of product transfer to the skin upon application. Such materials are generally disclosed in British Patent No. 1,291,819, published Oct. 4, 1972 and in U.S. Pat. No. 4,518,582 to Schamper et al., issued May 28, 1985, both of which are incorporated by reference herein.

A preferred benzylidene sorbitol for use in the present compositions is dibenzylidene monosorbitol acetal (DBMSA). This material is commercially available, such as Gell-All-D (manufactured by New Japan Chemical Co., Ltd.) and Millithix 925 (manufactured by Milliken Chemical, Division of Milliken & Company).

Polar Solvent

The polar solvent comprises from about 15% to about 75%, preferably from about 30% to about 50% of the total composition. Useful polar solvents include propylene carbonate, methanol, ethanol, n-propanol, n-butanol, 2-methoxyethanol, 2-ethoxyethanol; ethylene glycol, 1,2--propylene glycol, 1,3-propylene glycol, 1,4-butylene glycol, 1,2-butylene glycol, diethylene glycol, isopropanol, isobutanol, diethylene glycol monomethylether, diethylene glycol monoethyl ether, 1,3-butylene glycol, 2,3-butylene glycol, dipropylene glycol, 2,4-dihydroxy-2-methylpentane, and the like and mixtures thereof.

These solvents are fully described in the above-referenced U.S. Pat. No. 4,518,582 to Schamper et al., issued May 21, 1985. The preferred polar solvents are propylene carbonate, ethanol, propylene glycol, 1,3-butylene glycol and 2,4-dihydroxy-2-methylpentane (sometimes referred to as hexylene glycol) and mixtures thereof. Even more preferred solvents are propylene carbonate, ethanol and propylene glycol.

Most preferred is a mixture of propylene glycol and ethanol in a ratio of propylene glycol to ethanol of from about 0.5:1 to about 3:1, preferably from about 0.5:1 to about 2:1, in combination with from about 0.5% to about 3% of propylene carbonate.

Coupling Agents

The compositions of the present invention also essentially comprise at least one coupling agent. The term "coupling agent", as used herein, means any compound, composition, or combination thereof which acts to bring the polar, intermediate polarity and non-polar components of the present invention into a homogeneous stick composition. Preferred coupling agents include dimethyl isosorbide (which is commercially available from ICI Americas, Inc., Wilmington, Delaware as G-100 dimethyl isosorbide).

Other useful coupling agents include $C_6$–$C_{22}$ fatty alcohols, ethoxylated derivatives of $C_4$–$C_{22}$ fatty alcohols, propoxylated derivatives of $C_4$–$C_{22}$ fatty alcohols, and mixtures thereof as described, for example, in *Drug*

& *Cosmetic Industry*, 138 (2), p. 40 (1986), the disclosure of which is incorporated herein by reference. More preferred are ethoxylated derivatives of $C_{10}$-$C_{20}$ fatty alcohols, propoxylated derivatives of $C_{10}$-$C_{20}$ fatty alcohols, and mixtures thereof.

Still other useful coupling agents for use herein are polypropylene glycol ("PPG") ethers of $C_4$-$C_{22}$ (preferably $C_{10}$-$C_{20}$) fatty alcohols. Examples of such materials are: PPG-5-ceteth-20, PPG-4 myristyl ether, PPG-4 lauryl ether, PPG-10 cetyl ether, PPG-3 myristyl ether, and mixtures thereof. Additional examples are found in *CTFA Cosmetic Ingredient Dictionary*, Third Edition (Estrin et al., Editors; The Cosmetic, Toiletry and Fragrance Association, Inc.; 1982), pages 252–260 and 494–500, the disclosures of which are incorporated herein by reference in their entirety.

The coupling agent typically comprises from about 2% to about 30%, preferably from about 4% to about 20%, and most preferably from about 5% to about 15%, of the compositions of the present invention.

Buffering/pH Adjustment Agents

The compositions of the present invention further comprise from about 0.5% to about 10% of a buffering/pH adjustment agent. Suitable agents are generally disclosed in U.S. Pat. No. 4,346,079 to Roehl, issued Aug. 29, 1982 and in European Patent Application 175,074 of Schamper et al, published March 26, 1986, both of which are incorporated by reference herein.

Suitable buffering agents include coconut monoethanolamide, sodium aluminum chlorohydroxylactate, sodium hydroxide, stearamide monoethanolamide, acetamide MEA, zinc acetate, zinc stearate, aluminum oxide, calcium acetate, zinc oxide, magnesium oxide, calcium carbonate, calcium hydroxide, sodium carbonate, magnesium carbonate, zinc carbonate, butyrolactone, calcium oxide, and mixtures thereof.

Preferred buffering agents include coconut monoethanolamide, stearamide monoethanolamide, sodium aluminum chlorohydroxylactate and mixtures thereof. Most preferred buffering/pH adjustment agents are sodium aluminum chlorohydroxylactate, coconut monoethanolamide and mixtures thereof.

Optional Components

The compositions of this invention can also contain optional components which modify the physical characteristics of the gel sticks. Such components include hardeners, strengtheners, colorants, perfumes, emulsifiers, and fillers. Optional components, useful herein, are disclosed in the following patent documents, all incorporated by reference herein: U.S. Pat. No. 3,255,082, Barton, issued June 7, 1966; U.S. Pat. No. 4,137,306, Rubino, et al., issued Jan. 30, 1979; U.S. Pat. No. 4,279,658, Hooper, et al., issued July 14, 1981; and European Patent Specification 117,070, May, published Aug. 29, 1984.

The instant cosmetic sticks can also contain from about 0.1% to about 10% (by weight) or an inert filler material. Suitable filler materials include talc, colloidal slica (such as Cab-O-Sil, sold by Cabot Corp.), clays (such as bentonite), and mixtures thereof. The use of such fillers as stabilizing agents in cosmetic sticks is disclosed in U.S. Patent 4,126,679, Davy et al., issued November 21, 1978 which is incorporated by reference herein.

Method of Manufacture

The present invention also encompasses a process for the manufacture of a gel stick antiperspirant composition which is substantially free of unbound water comprising the steps of:

(a) preparing a premix comprising:
(i) from about 1% to about 40% of an antiperspirant active;
(ii) from about 10% to about 98% of water; and
(iii) from about 1% to about 40% of a polyhydric alcohol; removing said water thereby forming a solubilized antiperspirant active, and then heating the solubilized antiperspirant active to a temperature of from about 130° F. (54° C.) to about 165° F. (74° C.);

(b) preparing a main mix comprising the remaining components and heating said main mix to a temperature of from about 170° F. (77° C.) to about 225° F. (107° C.);

(c) combining said solubilized antiperspirant active and said main mix in a ratio of solubilized active to main mix of from about 1:19 to about 1:1 for from about 0.2 minutes to about 5 minutes; and (d) pouring said composition into stick form.

Preferably the premix is prepared by first dissolving the antiperspirant active in water and then adding the polyhydric alcohol.

The added water can be removed by any of a variety of methods known in the art such as, for example, heating the premix to a temperature of from about 70° F. (21° C.) to about 170° F. (77° C.), and/or under a vacuum of from about 10 to about 250 mm Hg.

Methods for Preventing Perspiration and Malodor

The present invention also provides methods for treating or preventing perspiration and malodor associated with human underarm perspiration. These methods comprise applying to the skin of a human a safe and effective amount of the antiperspirant gel of the present invention. The term "a safe and effective amount", as used herein, is an amount which is effective in eliminating or substantially reducing perspiration and malodor associated with human underarm perspiration while being safe for human use at a reasonable risk/benefit ratio.

The following examples further describe and demonstrate embodiments within the scope of the present invention. These examples are solely for the purpose of illustration and are not to be construed as limitations of the present invention as many variations are possible without departing from the spirit or scope thereof.

EXAMPLE 1

An antiperspirant composition of the present invention is made as follows:

| Step 1: Solubilized Antiperspirant Active | | |
|---|---|---|
| | Weight % | |
| Material | Initial Composition | Final Composition |
| Aluminum chlorohydrate[1] | 33.3 | 50.0 |
| Water | 33.4 | 0.0 |
| Propylene Glycol | 33.3 | 50.0 |
| | 100% | 100% |

The aluminum chlorohydrate is dissolved in the water at room temperature. The propylene glycol is then added to this solution and the added water is removed by heating under vacuum (45mm Hg at approximately 40° C.). The resulting solution is the "solubilized antiperspirant active".

Step 2: Antiperspirant Gel

| Material | Weight % |
|---|---|
| Solubilized Antiperspirant Active | 30.0 |
| Propylene Glycol | 16.2 |
| Propylene Carbonate | 1.0 |
| Ethanol | 18.3 |
| Dimethyl Isosorbide | 5.3 |
| PPG-5-Ceteth-20[2] | 2.0 |
| Di-isopropyl Adipate[3] | 16.0 |
| Isohexadecane | 4.0 |
| Sodium Aluminum Chlorohydroxy Lactate | 1.5 |
| Coconut MEA | 3.0 |
| Benzylidene Sorbitol[4] | 2.7 |
| | 100% |

[1]Westchlor DM200 by Westwood Chemical
[2]Procetyl AWS by Croda, Inc., 51 Madison Ave., New York, New York 10010
[3]Schercemol DIA by Scher Chemicals, Inc., Clifton, New Jersey 07012

The gel stick composition is prepared as follows. A premix is made by combining the propylene glycol, propylene carbonate, PPG-5-Ceteth, dimethyl isosorbide, di-isopropyl adipate, isohexadecane, and sodium aluminum chlorohydroxy lactate. These components are heated to approximately 160° F. (71° C.). The coconut MEA is then added and the resulting composition is mixed. The ethanol is then added and the mixture is cooled to about 85° F. (29.5° C.). The benzylidene monosorbitol is then added and the remaining mixture is heated to approximately 205° F. (96° C.) and then cooled to 190° F. (88° C.).

The solubilized antiperspirant active is simultaneously heated to 150° F. (65.5° C). The solubilized antiperspirant active is then added to the premix and the resulting combination is mixed for approximately 2 minutes. A uniform antiperspirant gel stick forms as the composition cools to room temperature. The resulting gel stick is optically clear with excellent efficacy as well as excellent nonsticky cosmetics and aesthetics.

The antiperspirant composition is applied to the underarm skin of a human to effectively prevent perspiration and underarm odor resulting from perspiration. The composition is relatively non-sticky and feels lubricious when applied to the skin.

Substantially similar results are obtained when the aluminum chlorohydrate is replaced, in whole or in part, by aluminum chloride, aluminum chlorhydroxide or a zirconium-aluminum glycine complex, or mixtures thereof.

EXAMPLES II - IV

These antiperspirant gel stick compositions are made as described above in Example 1.

| Material | II | III | IV |
|---|---|---|---|
| | Weight % | | |
| Solubilized Antiperspirant Active | | | |
| Propylene Glycol | (50) | (60) | (60) |
| Aluminum Chlorohydrate[1] | (50) | | |
| Aluminum Chlorohydrate[2] | | (40) | |
| Zirconium Aluminum[3] Trichlorohydrex Gly | | | (40) |
| Antiperspirant Gel | | | |
| Solubilized Antiperspirant Active | 20.0 | 25.0 | 25.0 |
| Propylene Glycol | 20.0 | 14.0 | 14.3 |
| Hexylene Glycol | — | 8.0 | — |
| Propylene Carbonate | — | 1.0 | 2.0 |
| Ethanol | 20.0 | 17.7 | 20.0 |
| Dimethyl Isosorbide | 8.0 | 7.0 | 10.0 |
| PPG-5-Ceteth-20[4] | — | — | 2.0 |
| PPG-10 Cetyl Ether[5] | — | 2.0 | — |
| Di-isopropyl Adipate[6] | 20.0 | 15.0 | 15.0 |
| Isohexadecane | — | — | 4.0 |
| Isopropyl Myristate | — | 4.0 | — |
| Cyclomethicone D-5[7] | 5.0 | — | — |
| Coconut Monoethanolamide | 3.0 | 3.0 | 1.0 |
| Stearamide Monoethanolamide | — | — | 3.0 |
| Sodium Aluminum Chlorohydroxy Lactate[8] | 1.0 | 0.8 | 1.0 |
| Benzylidene Sorbitol[9] | 3.0 | 2.5 | 2.7 |
| | 100% | 100% | 100% |

[1]Westchlor DM200 by Westwood Chemical
[2]Chlorhydrol by Reheis Chemical Company
[3]ZAGS by Reheis Chemical Company
[4]Procetyl AWS by Creda, Inc., 51 Madison Ave., New York, New York 10010
[5]Procetyl 10 by Croda Inc.
[6]Schercemol DIA by Scher Chemicals, Inc., Clifton, New Jersey 07012
[7]Supplied by GE Silicones
[8]Chloracel by Reheis Chemical Company, 235 Snyder Ave., Berkeley Heights, New Jersey 07922
[9]Millithix 915, manufactured by Milliken Chemical, Division of Milliken & Company

What is claimed is:

1. An antiperspirant gel stick composition which is substantially free of unbound water comprising:
   (a) from about 5% to about 50% of a solubilized antiperspirant active;
   (b) from about 7% to about 35% of intermediate polarity emollients;
   (c) from about 1% to about 5% of a benzylidene sorbitol;
   (d) from about 15% to about 75% of a polar solvent;
   (e) from about 1% to about 20% of dimethyl isosorbide; and
   (f) from about 0.5% to about 10% of a buffering agent.

2. An antiperspirant gel according to claim 1 wherein the solubilized antiperspirant active component is selected from the group consisting of basic aluminum salts, polyhydroxy derivatives, zinc and zirconium complexes of basic aluminum halides, zirconium-aluminum-glycine complexes, aluminum chlorohydroxide salts, and mixtures thereof.

3. An antiperspirant gel according to claim 2 wherein the polar solvent is selected from the group consisting of monohydric alcohols, polyhydric alcohols, propylene carbonate, and mixtures thereof.

4. An antiperspirant gel according to claim 3 wherein the buffering agent is selected from the group consisting of sodium aluminum chlorohydroxylactate, coconut monoethanolamide, stearamide monoethanolamide and mixtures thereof.

5. An antiperspirant gel according to claim 4 wherein the solubilized active is selected from the group consisting of aluminum chlorhydroxide salts, zirconium-aluminum-glycine complexes, and mixtures thereof.

6. An antiperspirant gel according to claim 5 wherein the polar solvent is selected from the group consisting of propylene carbonate, methanol, ethanol, n-propanol, n-butanol, 2-methoxyethanol, 2-ethoxyethanol; ethylene glycol, 1,2--propylene glycol, 1,3-propylene glycol, 1,4-butylene glycol, 1,2-butylene glycol, diethylene glycol, isopropanol, isobutanol, diethylene glycol, monomethyl ether, diethylene glycol monoethyl ether, 1,3-butylene glycol, 2,3-butylene glycol, dipropylene glycol, 2,4-dihydroxy-2-methylpentane, and mixtures thereof.

7. An antiperspirant gel according to claim 6 wherein the intermediate polarity emollient is selected from the group consisting of di-isopropyl adipate, di-n-butyl phtalate, diethyl sebacate, and ethyl ethyl carbomethyl phthalate, and mixtures thereof.

8. An antiperspirant gel according to claim 7 wherein the polar solvent is selected from the group consisting of propylene carbonate ethanol and propylene glycol and mixtures thereof.

9. An antiperspirant gel according to claim 8 wherein the benzylidene sorbitol is dibenzyl monosorbitol acetal.

10. An antiperspirant gel according to claim 9, which further comprises from 1% to 10% of a non-polar emollient.

11. The antiperspirant gel according to claim 10 wherein the non-polar emollient is selected from the group consisting of non-polar fatty acids and fatty alcohol esters hydrocarbons, volatile and non-volatile silicones and mixtures thereof.

12. A method for treating or preventing perspiration and malodor associated with human underarm perspiration, said method comprising applying to the skin of a human a safe and effective amount of an antiperspirant gel stick composition according to claim 1.

13. A method for treating or preventing perspiration and malodor associated with human underarm perspiration, said method comprising applying to the skin of a human a safe and effective amount of an antiperspirant gel stick composition according to claim 3.

14. A method for treating or preventing perspiration and malodor associated with human underarm perspiration, said method comprising applying to the skin of a human a safe and effective amount of an antiperspirant gel stick composition according to claim 7.

15. A method for treating or preventing perspiration and malodor associated with human underarm perspiration, said method comprising applying to the skin of a human a safe and effective amount of an antiperspirant gel stick composition according to claim 9.

16. A process for the manufacture of a gel stick antiperspirant composition which is substantially free of unbound water comprising the step of:
(a) preparing a premix comprising:
  (i) from about 1% to about 40% of an antiperspirant active;
  (ii) from about 10% to about 98% of water; and
  (iii) from about 1% to about 40% of a polyhydric alcohol; removing said water, thereby forming a solubilized antiperspirant active and then heating the solubilized antiperspirant active to a temperature of from about 130° F. (54° C.) to about 165° F. (74° C.);
(b) preparing a main mix comprising the remaining components and heating said main mix to a temperature of from about 170° F. (77° C.) to about 225° F. (107° F.);
(c) combining said solubilized active and said main mix in a ratio of solubilized antiperspirant active to main mix of from about 1:19 to about 1:1 for from about 0.2 minutes to about 5 minutes; and
(d) pouring said composition into stick form.

* * * * *

UNITED STATES PATENT AND TRADEMARK OFFICE
CERTIFICATE OF CORRECTION

PATENT NO. : 4,781,917
DATED : November 1, 1988
INVENTOR(S) : JOHN P. LUEBBE, PAUL R. TANNER, AND RICHARD D. FARRIS It is certified that error appears in the above-identified patent and that said Letters Patent is hereby corrected as shown below:

Front page of Patent  Assignee: "Proctor" should read --Procter--.

Column 1 line 22, "cosmetrically" should read --cosmetically--.

Column 5 lines 24-26, the formula $$\begin{matrix} CH_3 \\ [Si\!-\!O]_n \\ CH_3 \end{matrix}$$

should read

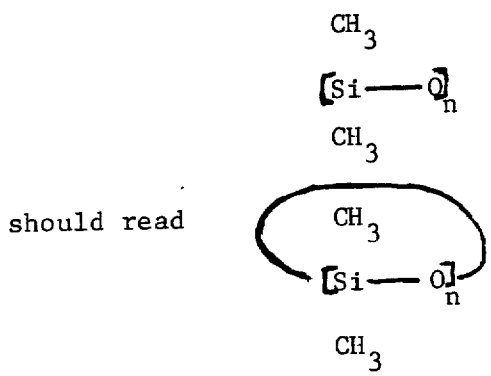

$$\begin{matrix} CH_3 \\ [Si\!-\!O]_n \\ CH_3 \end{matrix}$$

Column 9 line 20, footnote (4) is missing, it should read
--4 Millithix 925, manufactured by Milliken Chemical, Division of Milliken & Company.--

Signed and Sealed this

Twenty-third Day of January, 1990

Attest:

JEFFREY M. SAMUELS

*Attesting Officer*  *Acting Commissioner of Patents and Trademarks*